United States Patent [19]

Perry

[11] 4,311,483

[45] Jan. 19, 1982

[54] KINETIC METHOD FOR DIRECTLY DETERMINING TOTAL BILIRUBIN

[75] Inventor: Andrew W. Perry, LaHabra, Calif.

[73] Assignee: Beckman Instruments, Inc., Fullerton, Calif.

[21] Appl. No.: 138,062

[22] Filed: Apr. 21, 1980

Related U.S. Application Data

[63] Continuation-in-part of Ser. No. 49,769, Jun. 18, 1979, abandoned.

[51] Int. Cl.³ .................... G01N 33/50; G01N 33/72; G01N 33/52
[52] U.S. Cl. .................................. 23/230 B; 23/905
[58] Field of Search ............... 23/230 B, 905; 252/408

[56] References Cited

U.S. PATENT DOCUMENTS

| | | | |
|---|---|---|---|
| 3,314,977 | 4/1967 | Ertinghausen et al. | 23/230 B |
| 3,511,607 | 5/1970 | Green | 23/230 B |
| 3,682,586 | 8/1972 | Ertingshausen et al. | 23/230 B |
| 3,853,466 | 12/1974 | Rittersdorf et al. | 23/230 B |
| 3,923,459 | 12/1975 | Ertingshausen et al. | 23/230 B |
| 4,038,031 | 7/1977 | Lam | 23/230 B |
| 4,119,401 | 10/1978 | Sansur et al. | 23/230 B |

OTHER PUBLICATIONS

Landis et al., Clin. Chem. 24 (10) pp. 1700–1707, and 1690–1699 (1978).
Groso et al., Clin. Chem. 22 (4) 429–433 (1976).

*Primary Examiner*—Michael S. Marcus
*Attorney, Agent, or Firm*—R. J. Steinmeyer; John E. Vanderburgh; Robert S. Frieman

[57] ABSTRACT

A kinetic method for directly assaying total bilirubin in a sample. The kinetic assay entails mixing the sample to be assayed with an azo reagent and measuring the rate of formation of azobilirubin, wherein the rate of azobilirubin formation is directly proportional to the concentration of bilirubin in the sample being assayed. The azo reagent comprises a diazotized aromatic amine and accelerator and the composition and pH thereof is selected such that the rate constants for the conjugated and unconjugated reactions are approximately equal and such that the half-lives of both reactions are greater than 1 second and less tha 5 minutes.

4 Claims, No Drawings

KINETIC METHOD FOR DIRECTLY DETERMINING TOTAL BILIRUBIN

CROSS REFERENCE TO RELATED APPLICATION

This application is a continuation-in-part of application Ser. No. 049,769, filed June 18, 1979, now abandoned.

BACKGROUND OF THE INVENTION

1. Field of the Invention

The instant invention pertains to a kinetic method for directly determining total bilirubin.

2. Description of the Prior Art

The development of methodologies for the determination of bilirubin in biological fluids has been documented (1, 13). In general, endpoint techniques employing various accelerators and stabilized or unstabilized diazotized aromatic amines have been employed to measure total bilirubin (2–12 and 14–21).

Recently, Rizi et al. (22) disclosed a kinetic method for measuring conjugated bilirubin but still employed an endpoint technique to measure total bilirubin.

The reaction kinetics of conjugated and unconjugated bilirubin have been examined (23–25). More particularly, Landis et al. (24) discuss the kinetics of the reactions of unconjugated and conjugated bilirubin with p-diazobenesulfonic acid. Landis et al. (24) confirm that both the unconjugated bilirubin reaction and the conjugated bilirubin reaction each proceed in the following two steps, respectively:

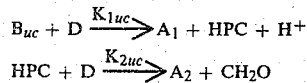  (I)
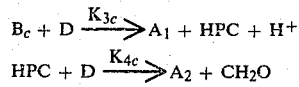  (II)

and $$B_c + D \xrightarrow{K_{3c}} A_1 + HPC + H^+ \quad (III)$$
$$HPC + D \xrightarrow{K_{4c}} A_2 + CH_2O \quad (IV)$$

wherein $B_{uc}$ is unconjugated bilirubin; $B_c$ is conjugated bilirubin; D is p-diazobenzenesulfonic acid; $K_{luc}$, $K_{2uc}$, $K_{3c}$, and $K_{4c}$ are the rate constants for reactions I through IV, respectively; $A_1$ and $A_2$ are azobilirubin isomers; and HPC is hydroxypyromethene carbinol. In the presence of an excess of p-diazobenzenesulfonic acid and in the absence of sulfanilic acid, Landis et al. (24) report that the reaction for either unconjugated or conjugated bilirubin proceeds in two successive first-order steps wherein $K_{luc} >> K_{2uc}$ and $K_{3c} >> K_{4c}$. Landis et al. (24) also report that in the presence of excess sulfanilic acid, $K_{2uc}$ approaches $K_{luc}$ and $K_{4c}$ approaches $K_{3c}$ and that the system exhibits complex kinetic behavior and is difficult to treat quantitatively.

In addition to the above, Landis et al. (24) also state that the reactions have half-lives in the range from 0.002 to 0.4 seconds (depending upon the reaction conditions) and, therefore, these authors employed a stopped-flow mixing system to achieve the needed mixing times.

In the second Landis et al. article (25), the authors describe a kinetic method that permits simultaneous determination of both unconjugated bilirubin and conjugated bilirubin in a single step in the same reaction mixture. This method makes use of the fact that at certain pH values, $K_{luc}$ differs significantly from $K_{3c}$, and this difference in $K_{luc}$ and $K_{3c}$ permits the two species to be resolved quantitatively by use of kinetic data.

Landis et al. (25) reason that the kinetic method for simultaneous determination of conjugated and unconjugated bilirubin would be more attractive in the immediate future if $K_{luc}$ and $K_{3c}$ were slow enough to be handled with conventional instrumentation. Caffeine concentration and pH are noted by Landis et al. (25) as being variables that might be manipulated to slow the reaction. However, Landis et al. (25) state that, unfortunately, the caffeine concentration used in their work was near its upper solubility limit. Landis et al. (25) conclude by pointing out that significant additional work is needed to evaluate the possibility that a pH below 5 could result in reactions slow enough to be monitored with conventional mixing systems and fast enough to give reasonable analysis times.

Despite the fact that reaction kinetics of conjugated and unconjugated bilirubin have been examined, no one has yet suggested a kinetic method for directly determining total bilirubin. This fact is significant in view of the extensive research undertaken in the area of bilirubin assays (26–37).

As known to those skilled in the art, kinetic methods for performing an assay have very significant advantages. These advantages include, but are not limited to, rapidity of the assay; freedom from interfering substances in the assay medium; and the ability to make accurate determinations without running blank reactions.

SUMMARY OF THE INVENTION

The instant invention encompasses a kinetic method for directly determining total bilirubin. In particular, the kinetic method for directly determining total bilirubin entails adjusting the overall rate constants of reactions I and II and reactions III and IV, namely:

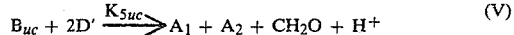  (V)

and

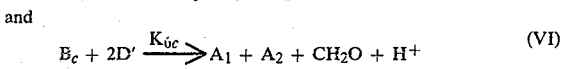  (VI)

wherein $B_{uc}$, $B_c$, $A_1$ and $A_2$ are as defined above; D' is a diazotized aromatic amine, and $K_{5uc}$ and $K_{6c}$ are the overall rate constants of reactions V and VI, respectively, such that $K_{5uc} \cong K_{6c}$. In addition, $K_{5uc}$ and $K_{6c}$ are adjusted such so that the half-lives of reactions V and VI are greater than or equal to 1 second, thereby enabling reactions V and VI to be handled with conventional instrumentation. This adjustment of $K_{5uc}$ and $K_{6c}$ is achieved by the appropriate selection of the accelerator and diazotized aromatic amine components of the azo reagent as well as the pH employed therein. Accordingly, the kinetic method comprises mixing a sample to be assayed with the azo reagent and measuring the rate of formation of azobilirubin ($A_1$ and $A_2$), wherein this rate of azobilirubin formation is directly proportional to the concentration of bilirubin in the sample being assayed.

DESCRIPTION OF THE PREFERRED EMBODIMENTS

The kinetic method for directly determining total bilirubin of the instant invention comprises mixing a sample to be assayed with an azo reagent comprising a diazotized aromatic amine and an accelerator and measuring the rate of formation of azobilirubin produced thereby, wherein this rate of formation is directly proportional to the concentration of total bilirubin in the sample being assayed. In order to perform this kinetic assay, it is essential to select the pH and the composition and concentration of the diazotized aromatic amine and the accelerator components of the azo reagent so that conjugated and unconjugated bilirubin react at substantially identical reaction rates, i.e., $K_{5uc} \cong K_{6c}$, with the diazotized aromatic amine component of the reagent. In addition to each of reactions V and VI having substantially the same reaction rates (and therefore substantially identical half lives), the half lives of these reactions should be of a magnitude greater than 1 second and less than 5 minutes. Preferably, the half-lives of reactions V and VI should be greater than 5 seconds and less than 2 minutes, more preferably less than 1 minute. Optimally, the half-lives of these reactions should be from about 10 to about 30 seconds. Reactions having half-lives of this magnitude can conveniently be measured on conventional spectrophotometric systems capable of measuring reaction rates as well as on the non-conventional stop flow analyzer. Conventional spectrophotometric instruments include, but are not limited to, centrifugal analyzers and rate colorimeters.

Several methods can be employed in the selection of the pH and the composition and concentration of the diazotized aromatic amine and accelerator components of the azo reagent of this invention. One such method entails separating a bilirubin sample into its conjugated and unconjugated bilirubin fractions and adjusting the ph and accelerator parameters by techniques known to those skilled in the art so that each bilirubin fraction yields substantially the same rate of reaction with the diazotized aromatic amine.

Another technique entails assaying bilirubin samples known to contain conjugated and unconjugated bilirubin fractions by an accepted endpoint technique and by the kinetic technique of this invention. Based upon this data one skilled in the art can then adjust the parameters of the azo reagent by techniques known to those artisans so that a satisfactory correlation between the endpoint assay and kinetic assay of this invention is obtained.

Virtually any diazotized aromatic amine and accelerator can be usd in the azo reagent employed in the kinetic assay of this invention as long as the conditions set forth above have been met.

Diazotized aromatic amines which can be employed in the instant invention include, but are not limited to, the diazo derivatives of the following compounds: sulfanilic acid, o-dianisidine, p-chloroaniline, 1,5-dichloroaniline, 2,4-dichloroaniline, 2-methoxy-4-nitroaniline, 1-aminoanthraquinone, p-nitroaniline and 4-chloro-methylaniline. Methods for forming the diazo derivatives of the above aromatic amines are well known to those skilled in the art (13) and therefore will not be elaborated upon herein.

The diazotized aromatic amines can also be stabilized by techniques well known to those skilled in the art (38). These stabilized diazotized aromatic amines include, but are not limited to, the boron tetrafluoride salt of the above diazotized aromatic amines, the 1,5-naphthalene disulfonic acid salt of the above diazotized aromatic amines, and the zinc chloride salts of the above diazotized aromatic amines.

Typical accelerators which can be employed in the azo reagent of the instant invention include, but are not limited to, alcohols containing one to five carbon atoms, alkylene polyols containing two to five carbon atoms, inorganic anions, nonionic surfactants, cationic surfactants, anionic surfactants and sulfoxides containing two to five carbon atoms. More particularly, the accelerator can be selected from a group consisting of caffeine salts, sodium benzoate, caffeine-sodium benzoate mixture, caffeine-sodium benzoate-sodium acetate mixture, diphylline, polyoxyethylene laurylether, ethanol, methanol, urea, gum arabic, ethylene glycol and dimethylsulfoxide.

In one embodiment of the instant invention, the azo reagent has a pH of about 2 and comprises 1 gm of the boron tetrafluoride salt of diazotized sulfanilic acid dissolved in 1 liter of 50% aqueous methanol.

In a preferred embodiment of the instant invention, the azo reagent has a pH of about 6 and comprises 1 gm of the boron tetrafluoride salt of diazotized sulfanilic acid and a caffeine(50 gm)-sodium benzoate(100gm) mixture dissolved in 1 liter of water.

In another preferred embodiment of the instant invention, the azo reagent has a pH of about 1.4 and comprises 4 gm of the boron tetrafluoride salt of diazotized sulfanilic acid dissolved in 1 liter of 30% aqueous dimethylsulfoxide.

The optimum time for measuring the rate of formation of azobilirubin generated in the kinetic assay of this invention will be determined by the type of instrument employed in making the measurement as well as by the pH and accelerator system present in the azo reagent employed therein. The measurement of the rate of formation of azobilirubin can be made with conventional kinetic clinical analyzers, e.g., centrifugal analyzers and rate colorimeters, as well as with stop flow analyzers. The rate of formation of azobilirubin usually will be made at least about 5 seconds after initiation of the reaction. Preferably, the measurement of the rate of formation of azobilirubin is made at least about ten seconds after initiation of the reaction. The maximum amount of time at which this measurement can be made is approximately five times the half life of the reaction. This time will vary depending upon the particular constituents of the azo reagent and the pH thereof. Typically, the maximum time for the measurement of the rate of formation of the azobilirubin produced by the reaction will be about two minutes after initiation thereof. Generally, the measurement of the rate of formation of the azobilirubin will be made up to about one minute after the initiation of the reaction. Preferably, the measurement of the rate of formation of the azobilirubin produced by the reaction will be made from about ten to about thirty, and more preferably from about ten to about twenty, seconds after the initiation of the reaction.

The following examples are provided for the purpose of further illustration only and are not intended to be limitations on the disclosed invention.

EXAMPLE 1

Reagents 5 gm caffeine
10 gm sodium benzoate
100 mg boron tetrafluoride salt of diazotized sulfanilic acid
1 N HCl

Protocol—Reagent Preparation

Caffeine (5 gm) and sodium benzoate (10 gm) were dissolved in deionized water to form an aqueous solution. Next boron tetrafluoride salt of diazotized sulfanilic acid (100 mg) was dissolved in the aqueous solution. The pH of the solution was adjusted to about 6 with 1 N HCl. The final volume was then adjusted to 100 ml with deionized water as required.

The various components of this reagent had been previously selected so that conjugated and unconjugated bilirubin reacted therewith at substantially identical reaction rates.

Protocol—Total Bilirubin Rate Assay

A Beckman brand Creatinine rate colorimeter Model No. 6641 (modified for use in measuring total bilirubin by changing its optical filter to read absorbance at 545 nm and by adjusting its circuitry to measure the reaction rate 15 seconds after the initiation of the reaction) was calibrated for total bilirubin by first assaying standard samples having a known bilirubin content. These standard samples were assayed by adding 25 $\mu$l of each standard to 1 ml aliquots of the above bilirubin reagent. The rate of change of absorbance in each reaction mixture was measured at 545 nm, 15 seconds after mixing the reagent with the standard sample. Based upon the result thereby obtained, the rate colorimeter was programmed to directly read in terms of bilirubin concentration.

After calibrating the rate colorimeter, each serum sample having an unknown bilirubin content was run in the same manner as were the standard samples. The results thereby obtained were read directly from the rate colorimeter. The results obtained from assaying the samples having an unknown bilirubin content are set forth in Table I.

EXAMPLE 2

Reagents 30 ml of dimethylsulfoxide (DMSO)
400 mg boron tetrafluoride salt of diazotized sulfanic acid
5 N HCl

Protocol—Reagent Preparation

DMSO (30 ml) was combined with 60 ml of deionized water to form an aqueous solution. The boron tetrafluoride salt of diazotized sulfanilic acid (400 mg) was then dissolved in this aqueous solution of DMSO. The pH of the resulting solution was adjusted to 1.4 with 5 N HCl. The final volume was then adjusted to 100 ml by adding deionized water as required.

The various components of this reagent had been previously selected so that conjugated and unconjugated bilirubin reacted therewith at substantially identical reaction rates.

Protocol—Total Bilirubin Rate Assay

A rate colorimeter used in Example 1 was calibrated for total bilirubin by first assaying standard samples having a known bilirubin content. These standard samples were assayed by adding 25 $\mu$l of each standard to 1 ml aliquots of the above bilirubin reagent. The rate of change of absorbance in each reaction mixture was measured at 545 nm, 15 seconds after mixing the reagent with the standard sample. Based upon the result thereby obtained, the rate colorimeter was programmed to directly read in terms of bilirubin concentration.

After calibrating the rate colorimeter, each serum sample having an unknown bilirubin content was run in the same manner as were the standard samples. The results thereby obtained were read directly from the rate colorimeter. The results obtained from assaying the samples having an unknown bilirubin content are set forth in Table II.

EXAMPLE 3

The samples of unknown bilirubin content which were assayed in Examples 1 and 2, samples 1-22 and 23-44, respectively, were also assayed for total bilirubin on a Technicon SMAC brand analyzer by the endpoint technique set forth in Technicon Technical Publication UA-0306B31, volume 2, Method No. SG4-0018PC6 (March, 1976). The results of these endpoint assays of samples 1-22 and 23-44 are set forth in Table I and Table II, respectively.

TABLE I

| Sample | End Point Value (X) (mg/dl) | Kinetic Value (Y) (mg/dl) |
|---|---|---|
| 1 | 0.5 | 0.50 |
| 2 | 0.8 | 0.76 |
| 3 | 0.1 | 0.26 |
| 4 | 0.6 | 0.52 |
| 5 | 10.6 | 10.79 |
| 6 | 8.6 | 8.59 |
| 7 | 1.5 | 1.42 |
| 8 | 0.4 | 0.43 |
| 9 | 0.9 | 0.84 |
| 10 | 1.5 | 1.39 |
| 11 | 0.5 | 0.45 |
| 12 | 6.9 | 6.71 |
| 13 | 1.3 | 1.20 |
| 14 | 0.3 | 0.30 |
| 15 | 0.3 | 0.26 |
| 16 | 0.5 | 0.53 |
| 17 | 1.0 | 1.06 |
| 18 | 2.5 | 2.65 |
| 19 | 1.6 | 1.59 |
| 20 | 0.2 | 0.21 |
| 21 | 0.9 | 0.82 |
| 22 | 1.5 | 1.40 |

Correlation
Y = A + B X
Intercept (A) = −0.02 mg/dl
Slope (B) = 1.00
$r^2$ = 0.9989
Means
X = 2.33 mg/dl
Y = 2.31 mg/dl
N = 22

TABLE II

| Sample | End Point Value (X) (mg/dl) | Kinetic Value (Y) (mg/dl) |
|---|---|---|
| 23 | 0.4 | 0.30 |
| 24 | 0.3 | 0.17 |
| 25 | 0.2 | 0.28 |
| 26 | 1.3 | 0.94 |
| 27 | 1.3 | 1.31 |
| 28 | 1.7 | 1.78 |
| 29 | 2.7 | 2.91 |
| 30 | 2.0 | 1.92 |
| 31 | 2.6 | 2.26 |
| 32 | 0.9 | 0.70 |
| 33 | 4.9 | 5.86 |
| 34 | 1.4 | 1.36 |
| 35 | 2.0 | 1.64 |
| 36 | 0.2 | 0.14 |
| 37 | 0.3 | 0.18 |
| 38 | 0.7 | 0.61 |

TABLE II-continued

| | | |
|---|---|---|
| 39 | 0.7 | 0.51 |
| 40 | 10.6 | 12.02 |
| 41 | 3.8 | 3.70 |
| 42 | 0.6 | 0.44 |
| 43 | 0.7 | 0.16 |
| 44 | 0.8 | 0.61 |

| Correlation | |
|---|---|
| Y = A + B X | |
| Intercept (A) | = −0.29 mg/dl |
| Slope (B) | = 1.15 |
| $r^2$ | = 0.9919 |
| Means | |
| X | = 1.81 mg/dl |
| Y | = 1.80 mg/dl |
| N | = 22 |

A comparison of the kinetic total bilirubin assays within the scope of this invention as set forth in Examples 1 and 2 with the endpoint assay of Example 3 is set forth in both Tables I and II. These tables show that the kinetic method of the instant invention for directly assaying total bilirubin shows excellent correlation with a reference endpoint technique of the prior art.

Based on this disclosure many other modifications and ramifications will naturally suggest themselves to those skilled in the art. These are intended to be comprehended as within the scope of this invention.

Bibliography

1. *The Monitor Jendrassik Bilirubin*, Lit. No. 39609-01, American Monitor Corp., Indianapolis, Indiana.
2. *Hycel Bilirubin Test*, Lit. No. 5753 Hycel, Inc., Houston, Texas.
3. U.S. Pat. No. 4,119,401.
4. Ertingshausen, et al., *Clin. Chem.* 19(12):1366-1369 (1973).
5. Borst et al., *Clinica Chimica Acta*, 55:121:128 (1974).
6. Kulhanek et al., *Clinica Chimica Acta*, 20:29-36 (1968).
7. Cross et al., *Clin. Chem.* 22(4):429-433 (1976).
8. Colombo et al., *Clinica Chimica Acta*, 51:217-219 (1974).
9. Colombo et al., *Clinica Chimica Acta*, 51:217-219 (1974).
10. Morin, *Clin. Chem.* 24(10):18 41-45 (1978).
11. Morin, *Clinica Chimica Acta*, 47:111-112 (1973).
12. Pearlman et al., *Clin. Chem.*, 20(4):447-453 (1974).
13. Henry et al., *Clinical Chemistry, Principles and Techniques*, 2d.Ed., Harper and Row, New York, N.Y. (1974) pp. 1037-1079.
14. Morin, *Clinica Chimica Acta*, 71:9-14 (1976).
15. *Centrifichem Methodology Sheet—Bilirubin Total*, Part No. 03001 Rev. 26, Union Carbide Corp., Clinical Diagnostics, Rye, N.Y.
16. Diagnostic Test Combinations Bilirubin *Colorimetric Method*, Boehringer-Mannheim Corp., N.Y., N.Y., Biochemica Test Combination, Boehringer-Mannheim Corporation.
17. Lolekha et al., *Clinical Chemistry*, 23(4):778-780 (1977).
18. Pearlman et al., *Clinical Chemistry*, 20(12):1538-1539 (1974).
19. Biggs et al., *Clinical Chemistry*, 21(3):449-450 (1975).
20. Dangerfield et al., *J. Clin. Path.*, 6:173-177 (1953).
21. Bartels et al., *Z. Klin. Chem. V. Klin. Biochem.*, 5:444-447 (1969).
22. Rizi et al., *Clinical Chemistry*, 23(6):1128 (1977).
23. Lathe et al., *J. Clin. Path.*, 11:155-161 (1958).
24. Landis et al., *Clin. Chem.* 24(10):1690-1699 (1978).
25. Landis et al., *Clin. Chem.*, 24(10):1700-1707 (1978).
26. U.S. Pat. No. 3,511,607.
27. U.S. Pat. No. 3,880,588.
28. U.S. Pat. No. 3,915,649.
29. U.S. Pat. No. 3,923,459.
30. U.S. Pat. No. 4,030,885.
31. U.S. Pat. No. 4,038,031.
32. U.S. Pat. No. 3,853,466.
33. U.S. Pat. No. 3,825,411.
34. U.S. Pat. No. 3,814,586.
35. U.S. Pat. No. 3,652,222.
36. U.S. Pat. No. 3,585,004.
37. U.S. Pat. No. 3,853,476.
38. Lillie, H. J. Conn's *Biological Stairs*, Williams & Wilkins Company, Baltimore, MA (1969), Ch VI.

The embodiments of the invention in which an exclusive property or privilege is claimed are defined as follows:

1. A kinetic method for directly determining total bilirubin comprising mixing a sample to be assayed with an azo reagent selected from a group consisting of
    (a) a composition having a pH of about 2 and comprising 0.1% w/v boron tetrafluoride salt of diazotized sulfonilic acid dissolved in 50% aqueous methanol;
    (b) a composition having a pH of about 6 and comprising 0.1% w/v boron tetrafluoride salt of diazotized sulfonilic acid and a caffeine (5% w/v) - sodium benzoate (10% w/v) mixture dissolved in water; and
    (c) a composition having a pH of about 1.4 and comprising 0.4 w/v boron tetrafluoride salt of diazotized sulfonilic acid dissolved in 30% aqueous dimethylsulfoxide;

and measuring the rate of formation of the azobilirubin produced by the reactions:

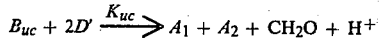

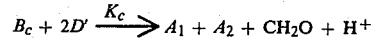

wherein
 $B_{uc}$ is unconjugated bilirubin;
 $B_c$ is conjugated bilirubin;
 $D'$ is a diazotized aromatic amine;
 $K_{uc}$ and $K_c$ are the rate constants for their respective reactions; and
 $A_1$ and $A_2$ are azobilirubin isomers;
wherein said rate of formation is directly proportional to the total concentration of bilirubin in said sample and wherein $K_{uc}$ is approximately equal to $K_c$ and wherein the half-lives of both reactions are greater than 1 second and less than 5 minutes.

2. The kinetic method of claim 1 wherein said azo reagent has a pH of about 6 and comprises 0.1% w/v boron totetrafluoride salt of daizotized sulfonilic acid and a caffeine (5% w/v) - sodium benzoate (10% w/v) mixture dissolved in water.

3. The kinetic method of claim 1 wherein said azo reagent has a pH of about 1.4 and comprises 0.4% w/v boron tetrafluoride sale of diazotized sulfonilic acid dissolved in 30% aqueous dimethylsulfoxide.

4. The kinetic method of claim 1 wherein said azo reagent has a pH of about 2 and comprises 0.1% w/v boron tetrafluoride salt of diazotized sulfonilic acid dissolved in 50% aqueous methanol.

* * * * *